(12) United States Patent
Gupta

(10) Patent No.: US 8,590,062 B2
(45) Date of Patent: Nov. 26, 2013

(54) PORTABLE PERSONALLY ATTACHABLE SYSTEMS FOR DELIVERING CONDITIONED AIR TO PERSONAL BREATHING ZONES AND OTHER BODY AREAS

(76) Inventor: Honey Gupta, Sherman Oaks, CA (US)

( * ) Notice: Subject to any disclaimer, the term of this patent is extended or adjusted under 35 U.S.C. 154(b) by 138 days.

(21) Appl. No.: 12/583,524

(22) Filed: Aug. 22, 2009

(65) Prior Publication Data

US 2011/0041237 A1 Feb. 24, 2011

(51) Int. Cl.
*A42C 5/04* (2006.01)

(52) U.S. Cl.
USPC ............. 2/171.3; 2/209.13; 2/195.1; 2/171.2

(58) Field of Classification Search
USPC .......... 2/171.3, 209.11, 209.13, 195.1, 171.2, 2/182.8, 209.14, 6.1, 5, 8.6, 425; 128/97.1, 200.28, 202.19
See application file for complete search history.

(56) References Cited

U.S. PATENT DOCUMENTS

| | | | | |
|---|---|---|---|---|
| 3,881,198 A | * | 5/1975 | Waters | 2/171.3 |
| RE33,286 E | * | 8/1990 | Waters | 2/171.3 |
| 5,425,620 A | * | 6/1995 | Stroud | 416/63 |
| 7,331,064 B1 | * | 2/2008 | Quintal | 2/209.13 |
| 7,921,473 B1 | * | 4/2011 | Winters | 2/171.3 |
| 2006/0053529 A1 | * | 3/2006 | Feher | 2/171.3 |
| 2010/0000007 A1 | * | 1/2010 | Wood | 2/171.3 |

* cited by examiner

*Primary Examiner* — Alissa Tompkins

(57) ABSTRACT

An apparatus for use in creating a zone of conditioned air on or near a person's body comprising: a blower unit configured to produce a flow of conditioned air; an air delivery system that is detachably connected to and is in flow communication with the blower unit, the said air delivery system having at least one outlet for discharging air.

3 Claims, 3 Drawing Sheets

PORTABLE PERSONALLY ATTACHABLE SYSTEMS FOR DELIVERING CONDITIONED AIR TO PERSONAL BREATHING ZONES AND OTHER BODY AREAS

TECHNICAL FIELD

The present invention recognizes a novel method of continuously delivering conditioned air, on or very near an individual's body, including breathing zones, whether, indoors or outdoors, by using a miniaturized, portable, and lightweight air conditioning and air delivery system that can be detachably attached to or integrated with personal apparels such as hats, caps, shoes, eye glasses, music listening devices, pieces of clothing such as shirt collars, button strips, men and women undergarments, pants, or specially designed support frames that can be attached to an individual's apparel or body. The conditioned air can be released anywhere, on or very near various areas of the body (for example, less than 1 foot from the body's surface), including, for example, the breathing zone (areas near nose and mouth), lower leg, hip, head, neck, and entire upper torso. The air conditioning system and the air delivering networks of ducts are so placed that they preferably are not visible when integrated with various apparels.

The present invention recognizes the vast need for providing relief to adults and children who suffer from respiratory disorders and allergies and therefore cannot enjoy the outdoors. The present invention also provides a solution to individuals seeking to defend themselves against viral infection or inhaling foul air while being in the company of those suffering from common cold and flu. Such situations arise especially when people travel in tight closed spaces such as in buses, trains, airplanes, or when they are a part of huge indoor or outdoor gatherings.

BACKGROUND

Asthma in the U.S. and around the world has increased at an alarming rate over the last 20 years and currently affects more than 15 million Americans. There is some speculation as to the cause of this increase, whether due to more time spent indoors in "tighter" homes with less fresh air or because of improvements in early diagnosis of disease. A recent study concluded that the risk due to residential allergen and pollutant exposure accounted for 39% of doctor-diagnosed asthma in U.S. children less than 6 years old. Currently an estimated 5,000,000 U.S. children (1 in 13) now suffer from asthma, accounting for 17% of all pediatric emergency room visits.

Allergic rhinitis or hay fever affects 40 million Americans. It can lead to rhinosinusitis (in 14% of the U.S. population) as well as otitis media (e.g. ear ache), the most common childhood disease requiring a healthcare visit.

In addition to the tremendous discomfort associated with these diseases and their all too often tragic outcomes (there are more than 5,000 asthma related deaths per year in the U.S.), the estimated annual cost of asthma in the U.S. is projected to be $14.5 billion this year, up from $6.2 billion only 10 years ago.

The first line of defense against these disease's symptoms recommended by allergists is to reduce environmental exposure. This can be accomplished by removing the allergen source (for example cats, cigarettes, molds, etc.), its reservoir (for example carpets, drapes, etc.) and also by cleaning the air through the use of high-efficiency air cleaners.

Use of air filtering systems based on High Efficiency Particulate Air (HEPA) filters, electrostatic precipitators, and others, are very effective in removing allergens and pollutants from the air, and consequently, when such an air is breathed in, it provides significant relief to individuals suffering from allergies, asthma, and other respiratory disorders. They are now routinely used in homes, hospitals, theatres, transport vehicles, equipments (vacuum cleaners), vents, exhausts, machinery, and many more places to clean air.

One of the major disadvantages of these air-filtering systems is that they are bulky and immovable and are therefore always installed inside homes, buildings, and vehicles by integrating them with the central air conditioning and heating systems. The same drawbacks reside with systems that deliver conditioned air directly to the breathing zones by integrating the air delivery system with the frame of a bed since the bulky blower unit has to be installed underneath the bed. Similarly, the portable fan-type room air cleaners are bulky enough to prevent an individual from carry them or tie them to his body. As such, these systems are incapable of providing a continuous flow of conditioned air to the personal breathing zone and other parts of the body while the individual is outdoors or moving.

The above information disclosed in this Background section is only for enhancement of understanding of the background of the invention and therefore it may contain information that does not form the prior art that is already known in this country to a person of ordinary skill in the art.

SUMMARY OF THE INVENTION

In certain embodiments of the present invention, an apparatus for use in creating a zone of conditioned air on or near a person's body including: a blower unit configured to produce a flow of conditioned air; an air delivery system that is detachably connected to and is in flow communication with the blower unit, the said air delivery system having at least one outlet for discharging air.

In certain embodiments of the present invention, an article of clothing having an apparatus for use in creating a zone of conditioned air on or near a person's body including: a blower unit configured to produce a flow of conditioned air; an air delivery system that is detachably connected to and is in flow communication with the blower unit, the said air delivery system having at least one outlet for discharging air formed therewith.

In certain embodiments of the present invention, an apparatus for use in creating a zone of conditioned air on or near a person's body including: a blowing means configured to produce a flow of conditioned air, wherein the blowing means comprises a power means to provide power to the blowing means; an attachment means configured to detachably attach the apparatus to a piece of clothing; and an air delivery means that is detachably connected to and is in flow communication with the blowing means unit, the said air delivery system having discharging means to discharge air.

These and other features, aspects and advantages of the present invention will become better understood with reference to the following drawings, description and claims.

Figure 1:
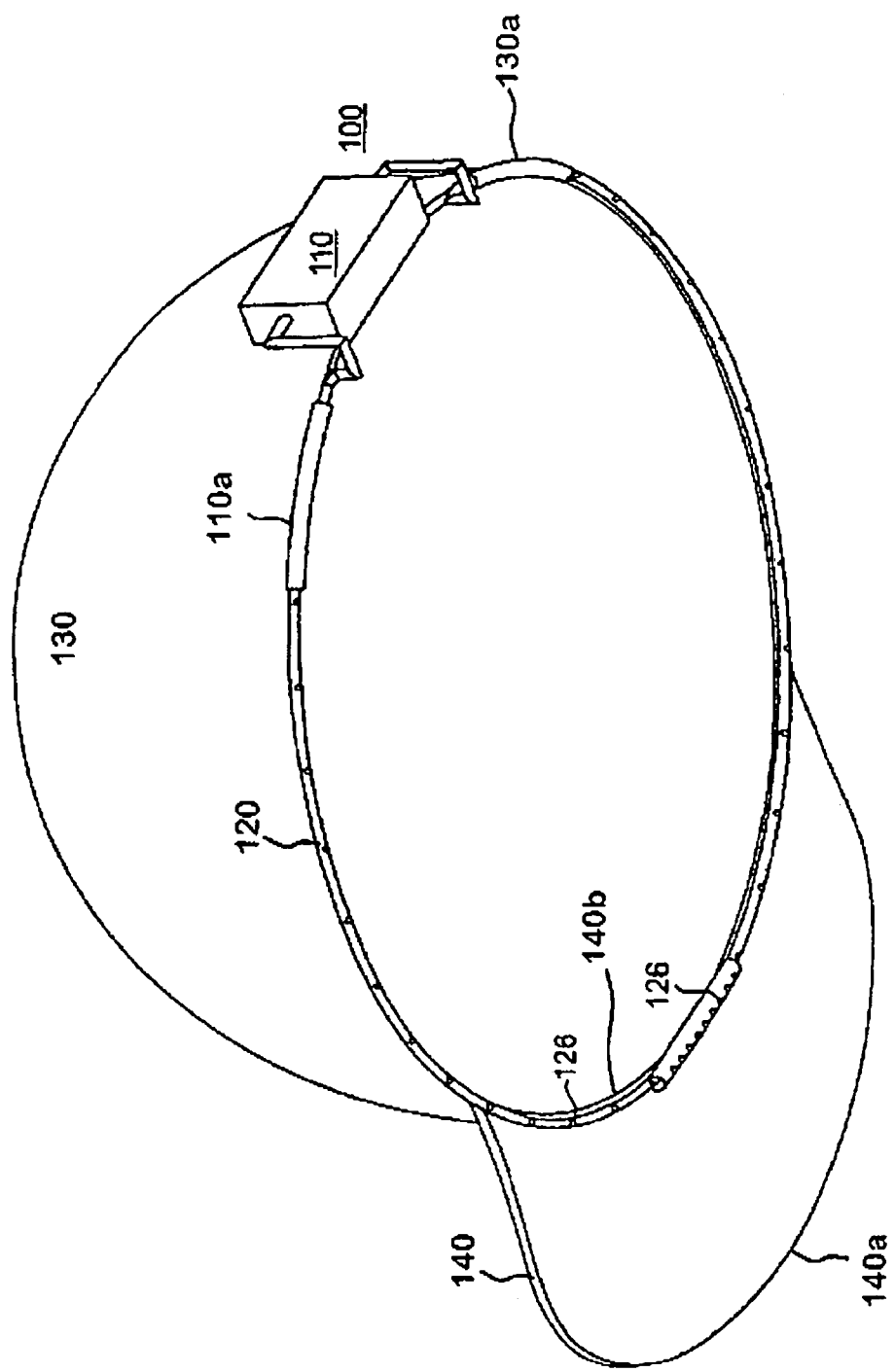
FIG. 1 illustrates an apparatus for use in creating a zone of conditioned air on or near a person's body 100 including a blower unit 110, comprising of an internal or external air filter 110a, and connected to an air delivery system 120 which has outlets/orifices 126 through which the air exits according to one embodiment of the present invention.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The following detailed description of example embodiments of the invention is not to be taken in a limiting sense, but is made merely for the purpose of illustrating the general principles of the invention, since the scope of the invention is best defined by the appended claims.

A novel approach that is recognized by the present invention is to miniaturize the air conditioning and air delivery system such that the system can be detachably attached to or permanently integrated with an individual's apparel such as caps, hard hats (for those working in the mining and construction business), shoes, glass frames, pieces of clothing (ties, shirt collars, and pleats of the trousers), etc. The system is so integrated that it is masked from the outside and cannot be noticed by others, whether in operation or idle. This way the individual enjoys a continuous flow of conditioned air very near his breathing zone, irrespective of whether he is indoors or outdoors, in a formal or causal setting, sitting, standing, walking or running, in a crowded gathering or sitting in a closed space in a train, bus or an airplane.

The invention recognizes the vast need for providing relief to adults and children who suffer from respiratory disorders and allergies and therefore cannot enjoy the outdoors. The invention also provides a solution to individuals seeking to defend themselves against viral infection or inhaling foul air while being in the company of those suffering from common cold and flu. Such situations arise especially when people travel in tight closed spaces such as in buses, trains, airplanes, or when they are a part of huge indoor or outdoor gatherings.

Referring now to the figures, FIG. 1 depicts an apparatus for use in creating a zone of conditioned air on or near a person's body 100 including a blower unit 110 connected to an air delivery system 120 which has orifices 126 through which the air exits according to one embodiment of the present invention. According to one embodiment of the present invention, air delivery system delivers air provided by the blower unit to a person's breathing zone and other areas of the body. According to one embodiment of the present invention, air delivery system is configured to be capable of sending conditioned air to various areas of the body, including the personal breathing zone. According to one embodiment of the present invention, air delivery system is configured to be capable of creating a zone of conditioned air around the person's head.

According to one embodiment of the present invention, air delivery system prevents allergens and other harmful particles from entering the zone of conditioned air, so that the air being breathed in by the person is substantially the conditioned air delivered by the delivery system. According to one embodiment of the present invention, air delivery system includes a blower unit that is preferably provided with a high efficiency filter, which filters the air prior to being delivered to the breathing zone. According to one embodiment of the present invention, air delivery system is configured to be able to condition air in other manners, such as heating or cooling the air, humidifying the air, introducing aromas and medicines into the air, and the like.

Figure 2:
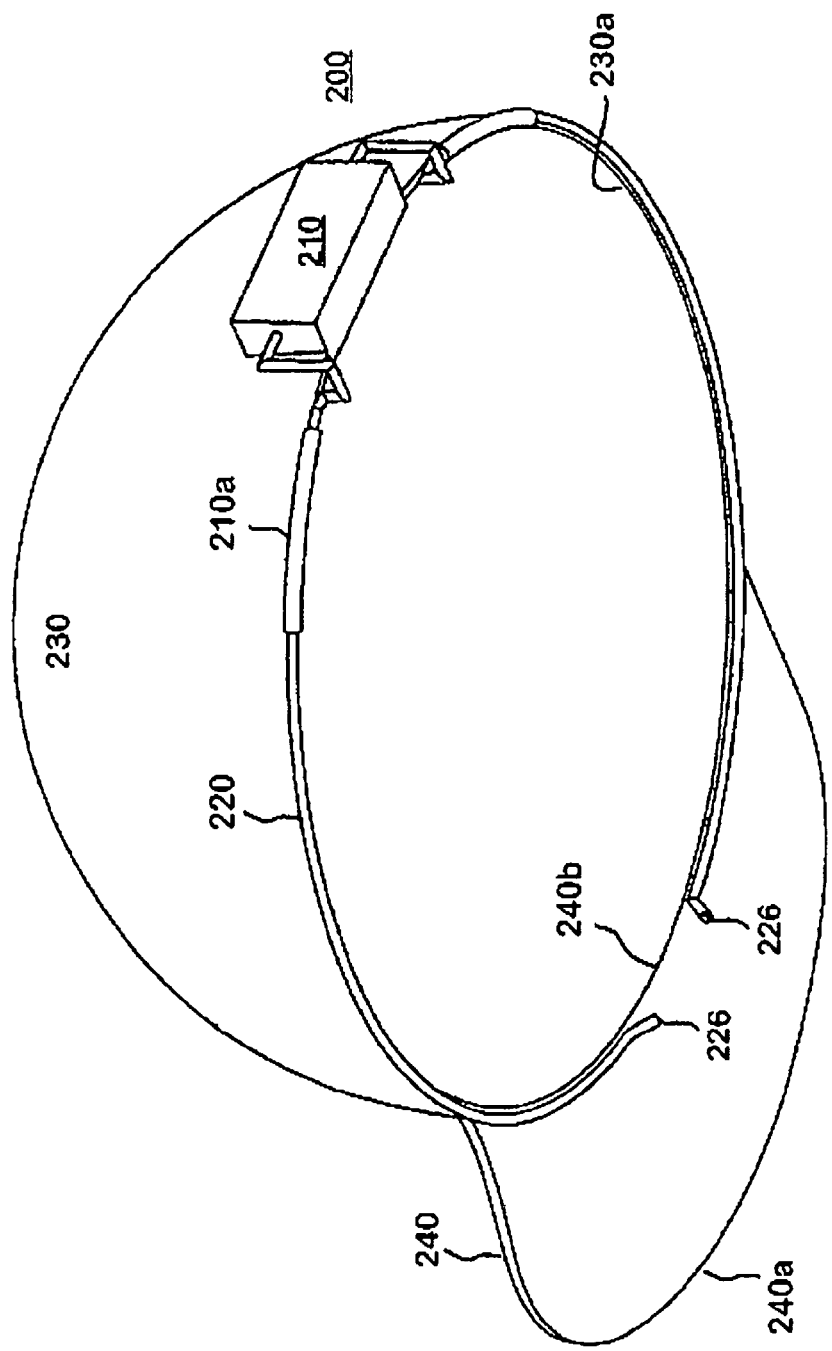
FIG. 2 illustrates an apparatus for use in creating a zone of conditioned air on or near a person's body 200 including a blower unit 210, comprising of an internal or external air filter 210a, and connected to an air delivery system 220 which has outlets/orifices 226 through which the air exits according to one embodiment of the present invention.

Referring now to the figures, FIG. 2 depicts an apparatus for use in creating a zone of conditioned air on or near a person's body 200 including a blower unit 210 connected to an air delivery system 220 which has outlets/orifices 226 through which the air exits according to one embodiment of the present invention. According to one embodiment of the present invention, air delivery system is configured with tiny holes/outlets/orifices over its lateral circumferential surface so as to allow delivery of conditioned air over a larger area, such as, delivering conditioned air around a person's head, neck, and into his breathing zone.

Figure 3:
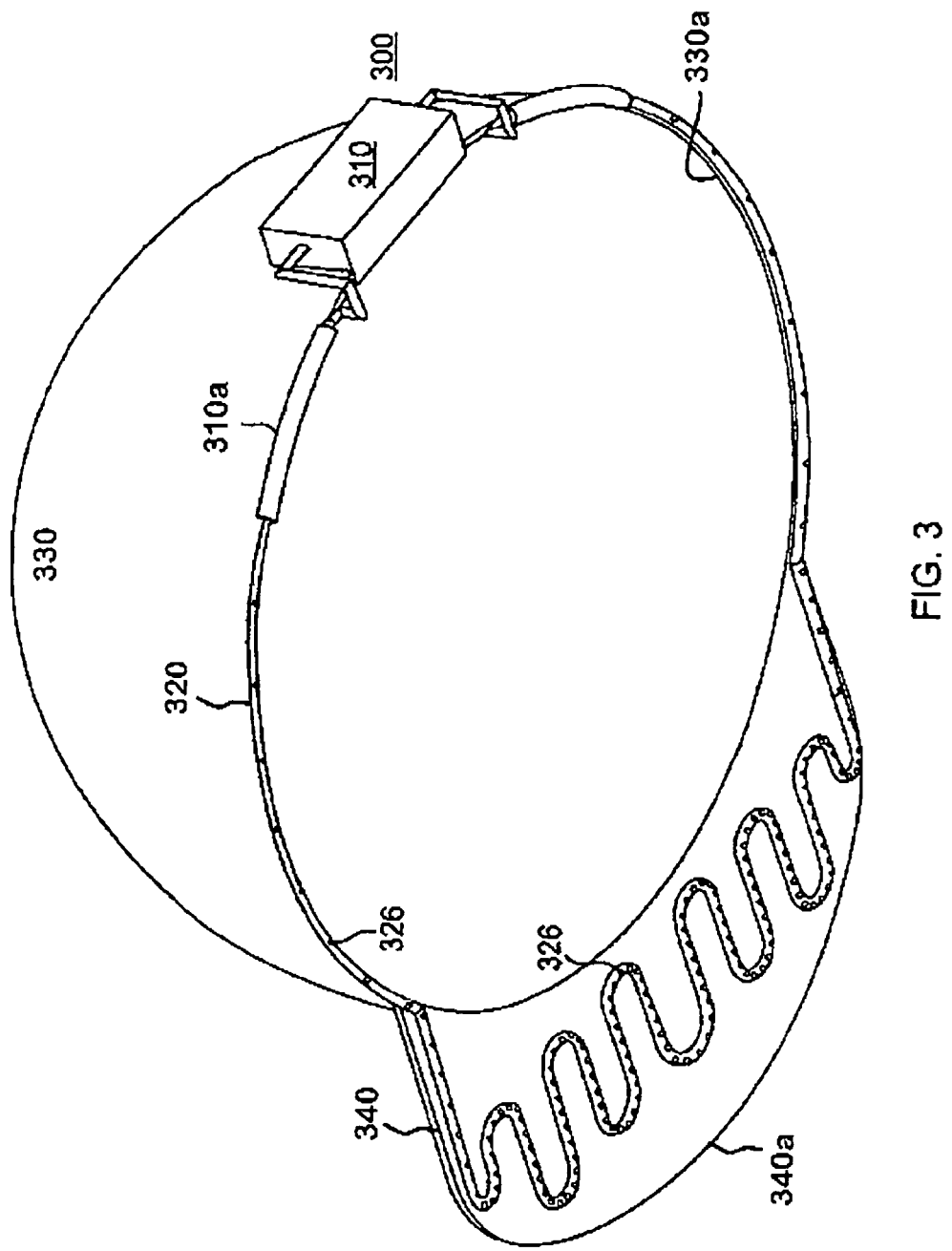
FIG. 3 illustrates an apparatus for use in creating a zone of conditioned air on or near a person's body 300 including a blower unit 310, comprising of an internal or external air filter 310a, and connected to an air delivery system 320 which has outlets/orifices 326 through which the air exits according to one embodiment of the present invention.

Referring now to the figures, FIG. 3 depicts an apparatus for use in creating a zone of conditioned air on or near a person's body 300 including a blower unit 310 connected to an air delivery system 320 which has orifices 326 through which the air exits according to one embodiment of the present invention. According to one embodiment of the present invention, air delivery system is configured with multiple air delivery ducts to distribute the conditioned air simultaneously to multiple areas.

According to one embodiment of the present invention, allergens and other harmful particles are prevented from entering the zone of conditioned air by use of a filter that is integrated with the blower unit. It can be either inside the body of the blower unit, or, as shown in FIGS. 1-3, the filter 110a, 210a, and 310a, can be located external to the body of the blower, with its one end releasably coupled to one of the air outlet ports of the blower unit. The other end of the blower unit's filter can be releasably snug fit to the air delivery tube/duct. Thus, the filter will be between the external body of the blower unit and the air delivery system, or in some cases integrated directly with the air delivery system. According to one embodiment of the present invention, since the apparatus for use in creating a zone of conditioned air on or near a person's body delivers conditioned air directly into a person's personalized breathing space, the air being breathed in by the person is substantially the conditioned air delivered by the air delivery system.

According to one embodiment of the present invention, blower unit includes a miniaturized, lightweight micro pump that preferably utilizes a low power-consuming motor that runs at imperceptibly low noise levels, does not heat up appreciably above the ambient when run over an extended periods of time, and can run on a 1.5V-12V DC battery that is widely available in retail stores. According to one embodiment of the present invention, blower unit is powered by a solar panel. According to one embodiment of the present invention, the flow rates of the pump should be such that when a reasonable diameter air delivery system having a duct (⅛ inch to ½ inch diameter) is used, the conditioned air exits the systems with a velocity between 10 and 100 feet per minute, a range in which skin sensation is known to be minimal.

Motor pumps with such attributes are widely available commercially. An example is a CTS diaphragm pump with coreless motor (E165-11-090) manufactured by Hargraves (Mooresville, N.C.), which weighs only 45 grams, has an overall dimensions of 1.27"×1.17"×0.8", and is DC powered with a 9 V battery. The pump is able to deliver a maximum volume of 1.6 liters/minute, which will yield exit velocities of over 600 feet per minute with a ⅛ inch diameter orifice and 73 feet per minute with an orifice of ⅜ inch in diameter. To keep the flow below 100 feet/minute, there is no need to operate the pump at its full capacity, which will increase pump and battery lives. While a number of such pumps are currently available from a number of vendors, the technology exists to further manufacture them in geometrical shapes that would conform to the specific piece of article to which the system is to be attached (hat, shoes, caps, glasses, etc.). Similarly it is foreseeable that given the large scope of the present invention that such vendors will be motivated to manufacture pumps that have longer lives that operate at imperceptibly (to normal human ear) low noise levels, and with an ability to further reduce their sizes and weights. The technology to make such modifications exists and the present invention can motivate them to deliver such new pump motors by taking advantage of mature miniaturized battery technology, noise management, lightweight materials, and brushless motors.

According to one embodiment of the present invention, blower unit includes a high efficiency filter which filters air prior to the air being delivered to the various personal zones identified above. The air can also be conditioned in other manners, for example, by one or more of heating or cooling the air, introducing aromas and medicines into the air, or simply pumping ambient air such as needed for heat-related relief during summer.

According to one embodiment of the present invention, a filter can be integrated with the air flow passage of the blower unit such that it resides inside the blower unit, or alternatively, it could be provided as an attachment to the exit port of the blower unit and just before the inlet section of the air delivering system. This construction allows for easier replacement of the filter. According to one embodiment of the present invention, the filter can be tube shaped with each end preferably shaped to snug fit into the exit port of the blower unit and the inlet port of the air delivering system.

According to one embodiment of the present invention, a filter can be integrated with the air delivery system such that it forms a concentric inner lining of the air delivery system. In this construction, the air can be conditioned as it travels through the air delivery system and this way conditioned air is delivered through an orifice of the air delivery system. According to one embodiment of the present invention, a distribution of orifices on the outer cylindrical surface of the air delivery system can be provided such that conditioned air can be released along the entire length or a section of the air delivery system after the air passes through the concentric filter.

According to one embodiment of the present invention, the filter can be either a high quality HEPA filter to stop pollutants and allergens, a charcoal filter to remove odors, or a specialized gas filter. According to one embodiment of the present invention, where only cooling or heating air is desired, a low quality filter or no filter can be provided in which case the air delivery duct can be directly snug-fitted into the outlet port of the blower unit. According to one embodiment of the present invention, a filter can contain medication, for example, to aid the opening of an individual's nasal passages, or injected with aromas for creating a pleasant environment.

According to one embodiment of the present invention, an apparatus for use in creating a zone of conditioned air on or near a person's body is integrated with a cap, hat, shoe, a pair of glasses, a pieces of clothing, or even with a fabric, depending upon the choice or constraints of the end user.

According to one embodiment of the present invention, an apparatus for use in creating a zone of conditioned air on or near a person's body is integrated with a cap/hat to create iCAP/iHAT (integrated cap/integrated Hat) or simply a hat/cap for generating and distributing a zone of filtered conditioned air on or near a head of a wearer. The hat comprises of a head covering portion having a crown portion 130 (230, 330), for covering a crown of the head of the wearer, the crown portion having a circumferential bottom edge 130a (230a, 330a) forming a perimeter portion. A brim 140 (240, 340) is attached to said crown portion having an outer perimeter portion 140a (240a, 340a) located on an outermost edge and an inner perimeter portion 140b (240b) shared with the perimeter portion of the crown where the brim is attached, wherein the brim is located above a face of the wearer when the hat is worn. In this embodiment, shown in FIGS. 1-3, as one of the examples, a blowing unit is attached to the crown portion and is configured to produce a flow of filtered conditioned air, wherein the blowing unit comprises a power unit which provides power to the blowing unit and an air filter to provide filtered conditioned air to the wearer.

An air delivery system comprising an air delivery tube 120 (220, 320) is detachably connected to the blowing unit and extends around the perimeter portion of the crown and at least a portion of the outer perimeter or the inner perimeter of the brim. The air delivery tube has a plurality of spaced outlets/orifices 126, 226, 326, wherein when the air delivery tube is connected to the blowing unit and its filter, a discharge of filtered conditioned air will exit the outlets at different locations along perimeter portions of the crown and brim allowing the wearer to breathe in the filtered conditioned air. As shown in FIG. 3, the air delivery tube with the plurality of spaced outlet can be arranged to cover an area of the brim extending outwardly from the perimeter portion of the crown, the brim configured to effectively provide coverage both in front and around a front portion of the face of the wearer. The outlets are so directed that the filtered conditioned air is released downwardly when the hat is worn.

The filter can be either inside the body of the blower unit, or, as shown in FIGS. 1-3, the filter 110a, 210a, and 310a, can be located external to the body the blower, with its one end detachably connected to the air outlet ports of the blower unit. The other end of the blower unit's filter can be detachably snug fit to the air delivery tube/duct. Thus, the filter will be between the external body of the blower unit and the air delivery system, or in some cases integrated with the air delivery system. The cap/hat discussed above can include a sports cap, a hat or a similar piece of apparel for use by individuals suffering from allergies, asthma other respiratory disorders and therefore provides relief when the wearer of the cap is outdoors. This could be particularly useful for school going children and college students suffering from asthma and allergies, which eventually lead to more serious medical condition such as rhinosinusitis and otitis media.

The cap/hat described above can be a hard hat of a worker for example as used in the mining, construction, railroad, gardening or waste management industry so that the wearer of the iHAT/iCAP can be protected from inhaling allergy-causing pollutants or small particles. According to one embodiment of the present invention, the filter can also include a gas absorber to protect a from inhaling unwanted gaseous pollutants and/or to allow a person to breathe clean, odor-free air. For this application, the blower unit can be installed anywhere on the hat with single or multiple ducts extending towards the front of the hat, preferably under the brim of the hat. An orifice can be located on the hat's brim in an area just above the nose of the wearer of the hat. According to one embodiment of the present invention, the conditioned air could also be discharged over an area of the brim by use of perforated outlets in the air delivery ducts that are spread over an area of the brim.

iCAPS can provide a low cost alternative for individuals who cannot afford more expensive central air filtering systems that are integrated with the central air conditioning and heating systems. iCAPS will also be useful to those who do have such systems installed inside their homes but cannot take full advantage of the system's cleaning abilities as the filtered air picks up allergens by the time it reaches the individual's immediate personal breathing zone. According to one embodiment of the present invention, the iCAP includes an apparatus for use in creating a zone of conditioned air on or near a person's body placed on a cap or hat and covered with matching fabric so that it is not visible from outside. The cover could be detachably replaced by use of Velcro for easy replacement of a battery and/or filter. According to one embodiment of the present invention, the air delivery system can be sewed inside the hat, either through the sides or other areas to bring it over the inside surface of the canopy where the conditioned air can be discharged in various manners as described for the iHAT.

According to one embodiment of the present invention, by placing the air outlet all around the circumference of the person's head, iCAPS can be designed to direct air towards the individual's neck and thereby provide relief from sweat during summers. Lack of air flow in areas where excessive sweat is accumulated is well known to cause skin irritation leading to skin reactions. The flow of air all around the neck and head region should help alleviate this condition.

According to one embodiment of the present invention, an apparatus for use in creating a zone of conditioned air on or near a person's body is integrated with a pair of glasses and is referred to as the iGLASSES (integrated glasses). According to one embodiment of the present invention, an iGLASSES includes an apparatus for use in creating a zone of conditioned air on or near a person's eyes or nose so that the wearer of the iGLASSES can be protected from inhaling allergy-causing pollutants or small particles. This embodiment can be useful for those in formal work environment where use of hats or similar apparels may not be desirable. Here the advancement in the pump technology, and battery (or solar panel) should allow manufacturing, of miniaturized pumps that can be placed and integrated with the frame of glasses. A preferred embodiment will be to place them at the end of the frame so that they remain masked behind the ears. According to one embodiment of the present invention, the conditioned air from the miniaturized blower can be delivered into the flow passage that is generated inside the hollow frame structure of the eyeglass. According to one embodiment of the present invention, the conditioned air can be delivered via a distribution of tiny holes provided at the base of the eyeglass bridge.

According, to one embodiment of the present invention, an apparatus for use in creating a zone of conditioned air on or near a person's body is integrated with a pair of shoes and is referred to as the iSHOES (integrated shoes). According, to one embodiment of the present invention, iSHOES can be used in office environment in lieu of iCAPS and iGLASSES. While this product will help those with respiratory disorders, use of just ambient air that is directed from shoes upwards into the trousers can provide significant relief for workers or people walking or working, outside during, summers. This can again provide excessive-sweat-related skin irritations that can occur in areas where the edges of undergarments snug-fit onto the skin areas of the thigh.

According, to one embodiment of the present invention, an apparatus for use in creating a zone of conditioned air on or near a person's body can be integrated in the heel of a shoe with delivery, ducts directing the conditioned air to the inside side surface of the shoe such that the conditioned air exits upwards inside the trousers. According to one embodiment of the present invention, an apparatus for use in creating a zone of conditioned air on or near a person's body delivers air through a network of ducts with one or more orifices located just below the area of the sole that normally protrudes outwards all around the shoe.

The word "conditioned air" in the specification and all the claims in this patent is used to mean, ambient air, filtered ambient air, filtered or ambient air with temperature above the ambient temperature, filtered or ambient air below the ambient temperature, air conditioned with aromatic odors, air conditioned with respiratory medication such as those helping open the nasal passage, etc. Therefore, the air conditioning systems in iHATS, iCAPS, iSHOES, and iGLASSES can circulate hot, cold, or just ambient air depending upon the weather condition and the choice of the user.

While conditioned air can be useful to individuals with respiratory disorders, an embodiment of the present invention can also be useful for defensive applications such as to those seeking protection against catching a cold or a flu virus. This could be particularly, useful for airline passengers that are subjected to a static air environment for long periods of time.

According to one embodiment of the present invention, iCAPS can provide clean air for individuals traveling in highly crowded trains and buses. According to one embodiment of the present invention, iCAPS can aid individuals such as waitresses or others working in an environment containing smoke who seek reduced exposure to smoking-related allergens can use iHATS, iCAPS, iSHOES or iGLASSES.

According to one embodiment of the present invention, one or more air delivery ducts can be integrated with the linings of men's and/or women's undergarments such that conditioned air can be discharged continuously or whenever desired to provide relief from heat or sweat that accumulates at the edges of the garments where they are snug-fit on the skin. Excessive sweat when combined with frictional rubbing during walking can cause skin irritation and in some case skin wounding, which is particularly a problem for obese people. This embodiment should provide significant relief to such individuals. For this purpose, according to one embodiment of the present invention the conditioned air could be just the flow of ambient air. According to one embodiment of the present invention, one or more air delivery ducts can be integrated within one or more shirt collars, pant pleats, etc., so as to provide continuous release of airflow in areas where frictional sliding and sweat accumulation can lead to skin irritation.

According to one embodiment of the present invention, an apparatus for use in creating a zone of conditioned air on or near a person's body can be physically integrated either within tables such as in restaurants, homes, and outdoors, and the system placed underneath the tables or within a network of ducts and orifices deployed over a region to deliver conditioned air over a part or entire surface of the table. This can be useful for providing an environment that is free of smoking-related allergens while eating, or the air can be simply conditioned with aromas for a more romantic environment.

According to one embodiment of the present invention, an apparatus for use in creating a zone of conditioned air on or near a person's body can be detachably attached to a picture frame, a computer frame, or other article(s) that are frequently placed on office tables to continuously supply conditioned air.

It should be understood, of course, that the foregoing relates to exemplary embodiments of the invention and that modifications may be made without departing from the spirit and scope of the invention as set forth in the following claims.

What is claimed is:

1. A hat for use in creating a zone of filtered conditioned air on or near a head of a wearer comprising:
   a head covering portion having a crown portion for covering a crown of the head of the wearer, the crown portion having a circumferential bottom edge forming a perimeter portion;
   a brim attached to said crown portion having an outer perimeter portion located on an outermost edge and an inner perimeter portion shared with the perimeter portion of the crown where the brim is attached, wherein the brim is located above a face of the wearer when the hat is worn;
   a blowing unit is attached to the crown portion by a mounting mechanism and is configured to produce a flow of filtered conditioned air, wherein the blowing unit comprises a power unit which provides power to the blowing unit and an air filter to provide filtered conditioned air to the wearer;
   an air delivery system comprising an air delivery tube detachably connected to the blowing unit and extending around the perimeter portion of the crown and at least a portion of the outer perimeter or the inner perimeter of the brim, the air delivery tube having a plurality of spaced outlets, wherein when the air delivery tube is connected to the blowing unit a discharge of filtered conditioned air will exit the outlets at different locations along the inner and outer perimeter portions of the hat allowing the wearer to breathe in the filtered conditioned air.

2. The hat of claim 1, wherein the plurality of spaced outlets are located at spaced intervals along the air delivery tube around the perimeter of the crown and brim and are configured to direct filtered conditioned air downwardly when the hat is located on the head of the wearer.

3. The hat of claim 1, wherein the plurality of spaced outlets are located at spaced intervals along the air delivery tube on the outer or inner perimeter of the brim, the outlets being arranged to cover an area of the brim extending outwardly from the perimeter portion of the crown, the brim configured to effectively provide coverage both in front and around a front portion of the face of the wearer, wherein the outlets are directed so that the filtered conditioned air is released downwardly when the hat is worn.

* * * * *